(12) United States Patent
Friese et al.

(10) Patent No.: US 8,608,315 B2
(45) Date of Patent: Dec. 17, 2013

(54) DEVICE AND METHOD FOR THE PRE-OPERATIVE SELECTION AND POSITION DETERMINATION OF AN ENDOPROSTHESIS

(75) Inventors: Thomas Friese, München (DE); Stephan Merk, München (DE)

(73) Assignee: Siemens Aktiengesellschaft, Munich (DE)

( * ) Notice: Subject to any disclaimer, the term of this patent is extended or adjusted under 35 U.S.C. 154(b) by 561 days.

(21) Appl. No.: 12/826,932

(22) Filed: Jun. 30, 2010

(65) Prior Publication Data

US 2011/0013148 A1 Jan. 20, 2011

(30) Foreign Application Priority Data

Jul. 16, 2009 (DE) .......................... 10 2009 003 446

(51) Int. Cl.
*G03B 21/26* (2006.01)
(52) U.S. Cl.
USPC ................................ 353/30; 353/71; 359/446
(58) Field of Classification Search
None
See application file for complete search history.

(56) References Cited

U.S. PATENT DOCUMENTS

| | | | |
|---|---|---|---|
| 2003/0067422 A1* | 4/2003 | Suyama et al. | 345/6 |
| 2003/0067587 A1* | 4/2003 | Yamasaki et al. | 353/30 |
| 2003/0216669 A1* | 11/2003 | Lang et al. | 600/587 |
| 2004/0150585 A1* | 8/2004 | Tomisawa | 345/6 |
| 2007/0063971 A1* | 3/2007 | Vecerina et al. | 345/156 |
| 2007/0162094 A1* | 7/2007 | Goldman et al. | 607/89 |
| 2008/0077003 A1 | 3/2008 | Barth et al. | |

FOREIGN PATENT DOCUMENTS

| | | |
|---|---|---|
| DE | 102004046151 A1 | 4/2006 |
| DE | 202008002159 U1 | 4/2008 |
| DE | 102007028639 A1 | 1/2009 |

OTHER PUBLICATIONS

Shahram Izadi et al., "Going Beyond the Display: A Surface Technology with an Electronically Switchable Diffuser," UIST '08, Proceedings of the 21$^{st}$ Annual ACM Symposium on User Interface Software and Technology, 2008, pp. 269-278.

* cited by examiner

*Primary Examiner* — Unsu Jung
*Assistant Examiner* — Saurel J Selkin
(74) *Attorney, Agent, or Firm* — Harness, Dickey & Pierce, P.L.C.

(57) ABSTRACT

A device and method for pre-operative selection and determination of a position of an endoprosthesis using a first rear projection screen with variable opacity and a movable second rear projection screen located in front of the first projection screen in respect of rear projection. The device may include a first projection unit for generating at least one first projection of the region of a subject in which an endoprosthesis is to be fitted, onto the first rear projection screen, and a second projection unit for generating at least one second projection of the endoprosthesis onto the second rear projection screen, the scaling of the first and second projection being identical. In an alternative embodiment, the second rear projection screen can be omitted.

15 Claims, 3 Drawing Sheets

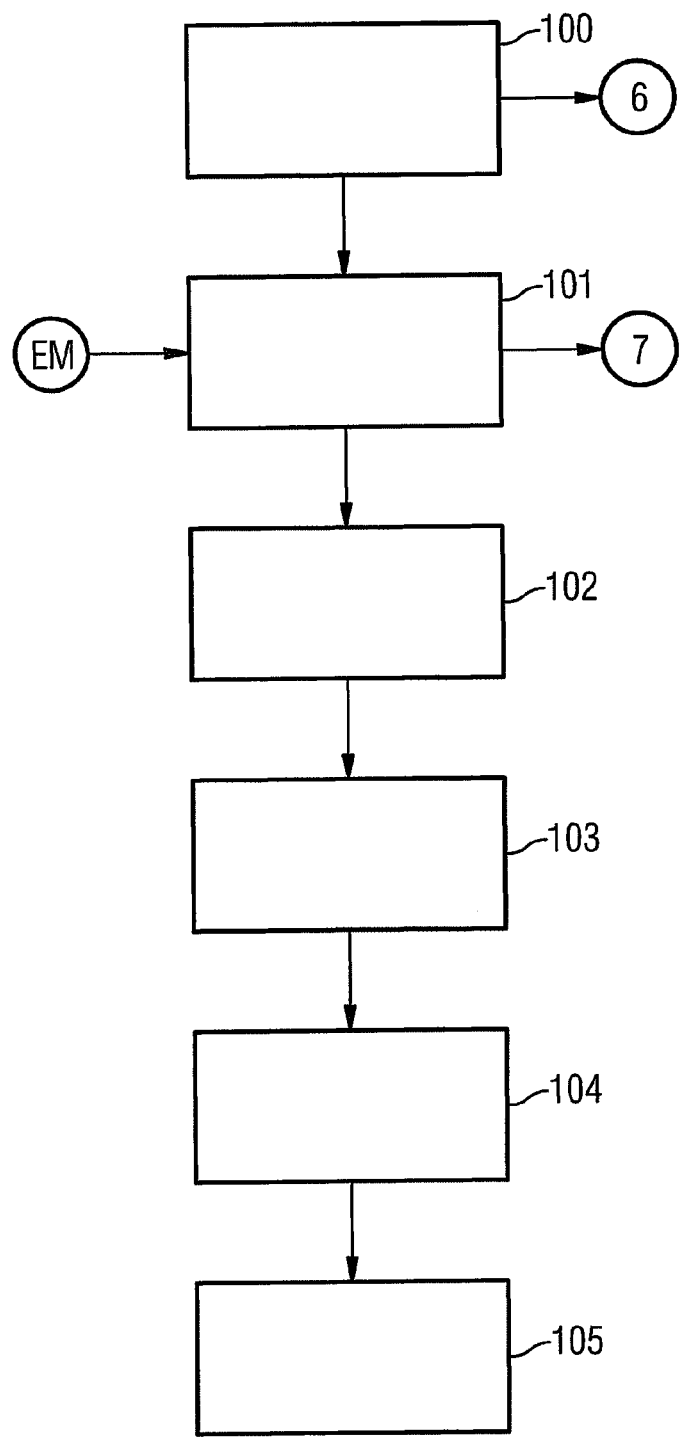

DEVICE AND METHOD FOR THE PRE-OPERATIVE SELECTION AND POSITION DETERMINATION OF AN ENDOPROSTHESIS

PRIORITY STATEMENT

The present application hereby claims priority under 35 U.S.C. §119 on German patent application number DE 10 2009 033 446.7 filed Jul. 16, 2009, the entire contents of which are hereby incorporated herein by reference.

FIELD

At least one embodiment of the invention generally relates to devices and to methods for the pre-operative selection and determination of a position of an endoprosthesis.

BACKGROUND

Known solutions for selecting an endoprosthesis and determining its position prior to a surgical intervention use a standard VDU workstation and fitting software in order to position, by mouse input, a graphical representation of endoprostheses in, for example, a relevant slice of a CT dataset or an X-ray photograph.

In clinical practice, the "fitting" of an endoprosthesis using the computer mouse is often experienced as unergonomic and laborious by physicians. They therefore use both a copy of the electronic image data on an X-ray film and templates of the different endoprostheses available in order to select a suitable endoprosthesis by manually moving different templates around on the X-ray film. This method will be referred to hereinafter as the "X-ray film/template technique". Although the decision concerning the selection of a particular endoprosthesis is recorded in a diagnostic findings report, the exact position of the endoprosthesis is not transferred to an X-ray image dataset in electronic form.

In "S. Izadi et al., Going Beyond the Display: A Surface Technology with an Electronically Switchable Diffuser; in Proceedings of User Interface Software and Technology 2008 (ACM UIST 2008)", the innovative "Second Light" screen display system is presented. "Second Light" uses an interactive display surface technology based on a switchable (rear) projection screen which can be made diffuse or transparent under electronic control.

A first projection screen is formed by the immovable surface of a housing and is designed as a diffuser which can be electrically switched to the modes "diffuse" or "clear" and is therefore used either as a projection screen or lets light pass through it. If switching between the two modes takes place at a high frequency that is imperceptible to the human eye (e.g. 100 Hz), during the clear phase an image can be projected through the first projection screen onto a second movable (rear) projection screen located above the first projection screen. The alternating transparency of the first projection screen also enables the manipulations (displacements, rotations) on the movable second projection screen to be tracked using a camera located below the first projection screen, and image processing software. Alternatively, manipulations (displacements, rotations) of the second projection screen could also be tracked by making the first projection screen touch-sensitive.

SUMMARY

At least one embodiment of the invention specifies a device and/or a method which provides improved pre-operative selection and improved pre-operative position determination of an endoprosthesis.

At least one embodiment of the invention relates to a device for the pre-operative selection and determination of a position of an endoprosthesis using a fixed first rear projection screen with variable opacity and a movable second rear projection screen located in front of the first rear projection screen in respect of rear projection. The device also comprises a first projection unit for generating at least one first projection of a region of a subject, e.g. a patient, in which the endoprosthesis is to be fitted, onto the first rear projection screen, and a second projection unit for generating at least one second projection of the endoprosthesis onto the second rear projection screen, the scaling of the first and second projection being identical. An advantage of at least one embodiment of the invention is that fitting is possible in any slice plane and that the experience of users of an X-ray film/template technique can be applied.

In a further development of at least one embodiment of the invention, the second projection through the first rear projection screen can take place by varying the latter's opacity, thereby making a second projection easily visible.

At least one embodiment of the invention also specifies a device for the pre-operative selection and positioning of an endoprosthesis using a single fixed first rear projection screen. The device again comprises a first projection unit for generating at least one first projection of a region of a subject, e.g. a patient, in which the endoprosthesis is to be fitted, onto the first rear projection screen, and a second projection unit for generating at least one second projection of the endoprosthesis onto the first rear projection screen, the scaling of the first and second projection being identical. The advantage here is that only one rear projection screen is used.

In another embodiment, a displacement unit for shifting and/or rotating the second rear projection screen or the second projection with respect to the first rear projection screen can be used. The advantage of this is that the two projections can be easily moved relative to one another.

In addition, the displacement unit can incorporate a feedback unit by which the force required for moving the second rear projection screen or the second projection can be varied. This provides the advantage of intuitive haptic control for the selection and position planning of an endoprosthesis.

The first projection can also be a two-dimensional projection of a captured image or image slice of the region of interest.

In a further development, the second projection can be a two-dimensional projection of a pictorial and/or geometric sectional view of the endoprosthesis.

In another embodiment, the first projection can be generated from an X-ray photograph or a slice of a tomography dataset and/or the second projection can be generated from a three-dimensional geometry dataset of the endoprosthesis.

In addition, the device can incorporate a prosthesis projection control unit for selecting the second projection, the first and the second projection having a common image capture plane.

The device can also have a zoom control unit for simultaneous zooming of the first and second projection.

In a further development, the device can incorporate a simultaneous projection control unit for simultaneously varying and/or selecting the image capture plane of the first and second projection.

In another embodiment, the device can have a prosthesis selection control unit for selecting an endoprosthesis from stored data.

At least one embodiment of the invention relates to a method for the pre-operative selection and determination of a position of an endoprosthesis by generating at least one first projection onto a first rear projection screen with variable opacity of the region of a subject in which the endoprosthesis is to be fitted, and by generating at least one second projection of the endoprosthesis through the first projection screen onto a movable second rear projection screen, the scaling of the first and second projection being identical.

At least one embodiment of the invention also specifies a method for the pre-operative selection and determination of a position of an endoprosthesis by generating at least one first projection onto a first rear projection screen of the region of a subject in which the endoprosthesis is to be fitted, and by generating at least one second projection of the endoprosthesis onto the first projection screen, the scaling of the first and second projection being identical.

In a further development, at least one embodiment of the method can include displacing and/or rotating the second rear projection screen or second projection relative to the first rear projection screen so that the second projection is fitted into the first projection.

At least one embodiment of the method can also include storage of the designation of the endoprosthesis and of the position in respect of the first projection. The advantage of this is that accurate documentation for a subsequent surgical intervention is possible.

BRIEF DESCRIPTION OF THE DRAWINGS

Further special features and advantages of the invention will emerge from the following explanations of a plurality of exemplary embodiments and with reference to the accompanying schematic drawings in which:

FIG. 3: shows a flowchart of a method for the pre-operative selection and position determination of an endoprosthesis.

DETAILED DESCRIPTION OF THE EXAMPLE EMBODIMENTS

Figure 1:
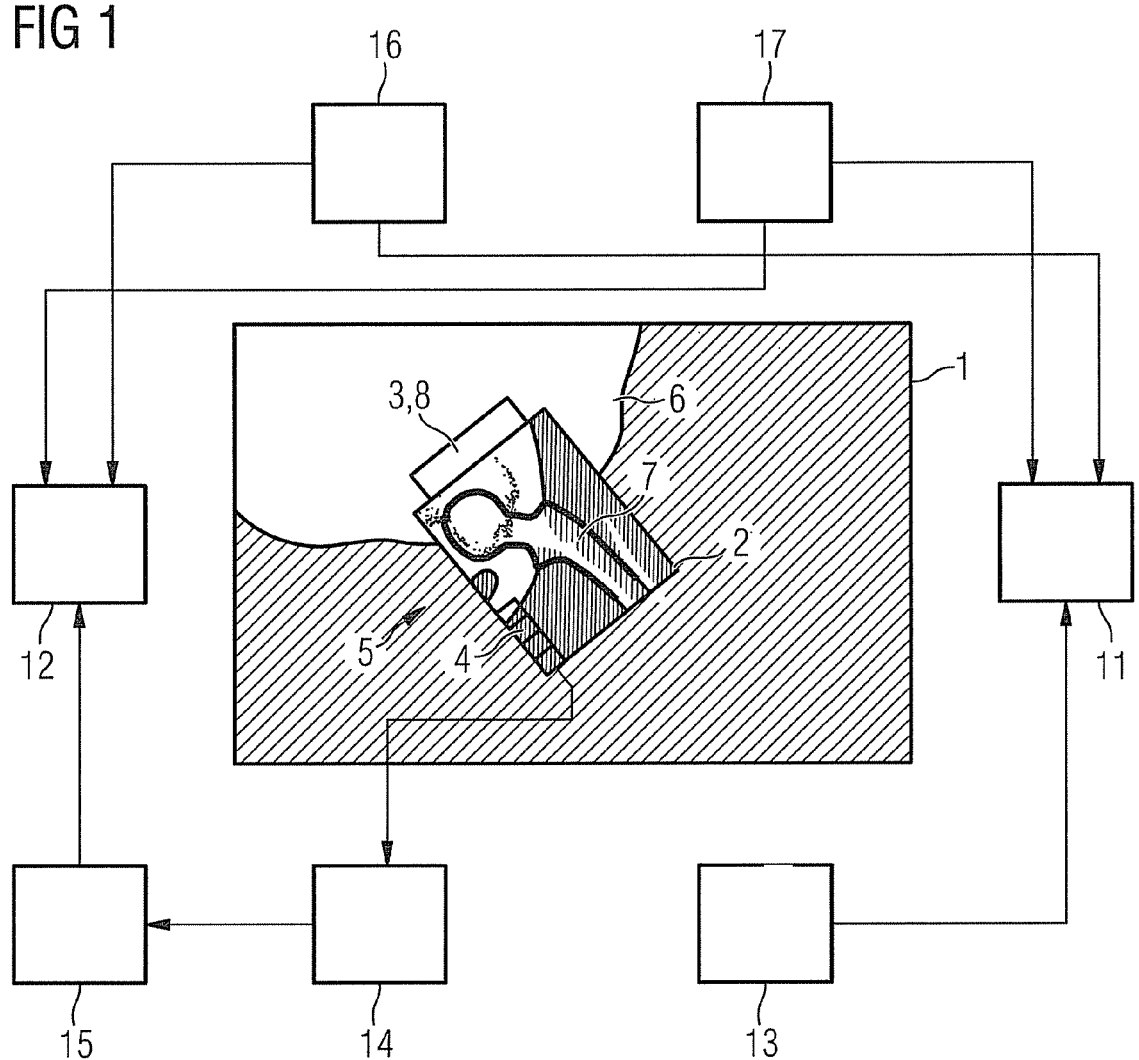
FIG. 1: shows a block diagram of a device for the pre-operative selection and position determination of an endoprosthesis.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows a block diagram of a device for the pre-operative selection and position determination of an endoprosthesis. The device comprises a fixed first rear projection screen 1 with variable opacity and a second rear projection screen 2 which is in front of the first rear projection screen 1 in respect of rear projection and can be moved relative thereto. The second projection screen 2 is connected to a displacement unit 8 for rotation and shifting and to a feedback unit 3. The feedback unit influences the displacement resistance of the second projection screen 2 on the first projection screen 1, e.g. in accordance with the operating principle of force-feedback mice, and can therefore provide a user with haptic feedback for moving the second projection screen 2. In addition, the second projection screen 2 can be connected to elements 4 for controlling, i.e. rotating and shifting the second projection unit, such as switches, trackballs, etc. Alternatively, such control elements 4 can also be projected onto the second projection screen 2 and their "operation" captured by a camera below the first projection screen 1. The second projection screen, feedback unit 3 and control elements 4 constitute the so-called handset 5.

The feedback unit 3 makes it easier or harder to move the handset 5 in particular directions. By making it easier, the user can be guided in the direction of suitable fits. By making it harder, the user receives haptic feedback about poor or impossible fits (e.g. if the head of a hip joint endoprosthesis overlaps a bony structure in the current configuration). Such force-feedback assistance for the user requires the extraction of relevant structures (e.g. acetabulum and endoprosthesis contour in the case of hip joint endoprostheses) from an anatomy projection 6 and a prosthesis projection 7 with the aid of suitable image processing algorithms (e.g. edge detection) and using suitable collision and movement planning algorithms. As an alternative to the automatic detection of relevant anatomical structures, the user can also mark them with a finger on the first rear projection screen 1 so that they can be displayed and used by the device.

The first projection screen 1 and the handset 5 with the second projection screen 2 are logically assigned two 2D-coordinate systems (not shown in FIG. 1) which the device user can shift and rotate against one another by moving the handset 5.

By way of a first projection unit 11, a two-dimensional first projection 6, hereinafter referred to as an anatomy projection, of a suitable X-ray photograph, e.g. an AP photograph of the pelvic region in the case of selecting and fitting a hip joint endoprosthesis, or of a suitable slice (either native or reconstructed slice) from a tomography dataset (CT, MRI), is projected onto the first projection screen 1.

Using an anatomy projection control unit 13, the slice plane through the anatomical structures can be selected and/or changed (displacement, rotation), if the anatomy projection is a slice through a tomography dataset or has been calculated from same. The anatomy projection control unit 13 can comprise a trackball and buttons, for example, or can be implemented as a virtual control on a section of the first projection screen 1.

With the aid of a prosthesis selection control unit 14, an endoprosthesis model can be selected form a large number of endoprosthesis models. The prosthesis selection control unit 14 comprises, for example, a selection menu projected onto a section of the first projection screen 1.

Using a second projection unit 12, a two-dimensional second projection 7, hereinafter referred to as a prosthesis projection, of a suitable slice through the endoprosthesis model, said slice being calculated from the 3D geometry model of a selected endoprosthesis model and matched to the scaling of the anatomy projection 6, is projected onto the second projection screen 2 of the handset 5.

By way of a prosthesis projection control unit 15, the endoprosthesis model selected is rotated in space relative to the anatomical structures and a slice plane through the endoprosthesis model selected and positioned in space is selected. The prosthesis projection control unit 15 typically comprises a trackball and buttons or a virtual control on a section of the first rear projection screen 1.

With the aid of a zoom control unit 16, the anatomy and prosthesis projection 6, 7 can be zoomed simultaneously (zoom-in, zoom-out). The zoom control unit 16 can comprise, for example, elements projected onto a section of the first projection screen 1.

Using a simultaneous projection control unit 17, the slice plane through the anatomy and the prosthesis model can be selected and/or changed simultaneously (displacement, rotation). The simultaneous projection control unit 17 can typically comprise a trackball and buttons or be projected onto a section of the first rear projection screen 1 as a virtual control.

In another embodiment of the device, the first projection 6 of the anatomical structures onto the first rear projection screen 1 and the second projection 7 of the endoprostheses onto the second rear projection screen 2 can be three-dimensional, thereby simplifying endoprosthesis selection and coarse fitting by displacement of the handset 5 and rotation in space using the prosthesis projection control unit 15. In order to constantly provide the user with a view of the available space in which fitting is to take place, the structures in the user's line of sight are either automatically removed or displayed semi-transparently in the three-dimensional representation. However, as a three-dimensional representation always has perspective distortions, the possibility of fine fitting in 2D must always exist.

In another embodiment, the second rear projection screen 2 in the handset 5 can be dispensed with. The latter then merely constitutes an input device whose position is detected to control the system and which if necessary provides force-feedback to the user, both anatomical structures and the endoprosthesis being projected onto the first rear projection screen 1, and the representation of the endoprosthesis being embedded in the anatomical structures by the system software and jointly projected.

In another embodiment, the second rear projection screen 2 and the handset 5 can be dispensed with. Instead, a virtual handset is projected together with the prosthesis projection 7 onto the first rear projection screen 1 and can be moved by the user relative to the anatomy projection 6 likewise projected onto the first rear projection screen 1. The user does this by positioning e.g. two fingers at opposite corners of the virtual handset and moving it by synchronous dragging of the finger over the surface. Said representation of the virtual handset and of the endoprosthesis is embedded in the anatomical structures by the device software and projected onto the first rear projection screen 1. However, force-feedback is not possible in this embodiment.

The device can also be used for fitting components e.g. into CAD applications, the component to be fitted being projected onto the handset 5 and the system into which the component is to be fitted being projected onto the first rear projection screen 1.

Figure 2:
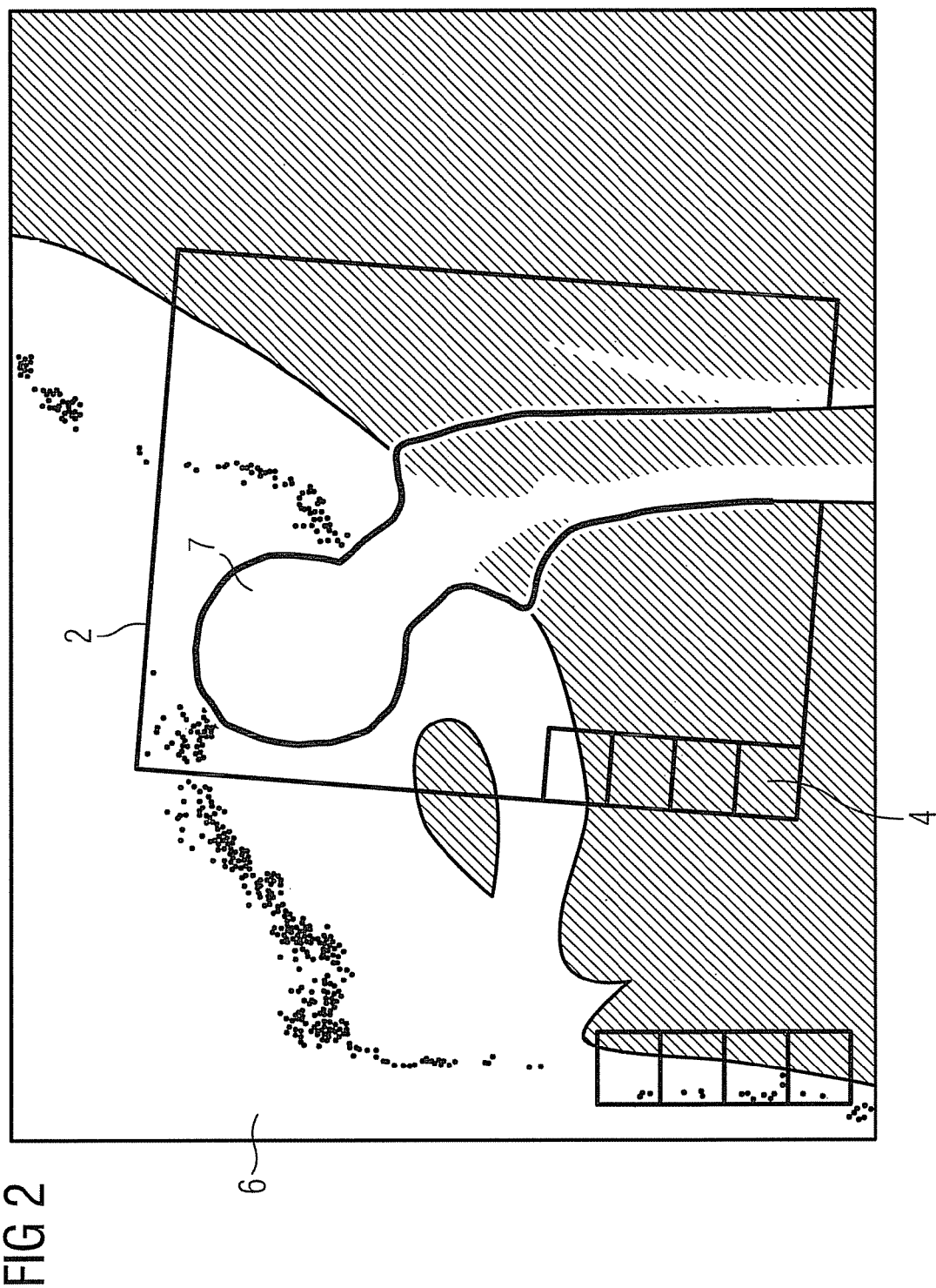
FIG. 2: shows a first and second projection

A first projection 6, the so-called anatomy projection, and a second projection 7, the so-called prosthesis projection, are illustrated in FIG. 2. The anatomy projection 6 shows part of a human pelvis and is displayed on the first rear projection screen 1. The prosthesis projection 7 shows the geometry of an endoprosthesis and is displayed on the second rear projection screen 2. The movement of the second rear projection screen 2 is controlled using the virtual elements 4.

FIG. 3 shows a flowchart of an inventive method of an embodiment for the pre-operative selection and position determination of an endoprosthesis, comprising steps 100 to 105.

In step 100, a user loads an image dataset of a region of a patient in which an endoprosthesis is to be fitted, and generates a first projection 6 (anatomy projection) on a first rear projection screen 1. If the dataset is a tomography dataset, the user selects using the anatomy projection control unit 13 an anatomy projection 6 which is projected onto a first projection screen 1. Alternatively, a default anatomy projection can already be proposed by the device (e.g. AP slice at the level of the head of the femur in the case of a hip joint endoprosthesis).

In step 101, on the basis of an assessment of the anatomy projection 6 selected and his experience, the user selects using a prosthesis selection control unit 13 an endoprosthesis model EM which is projected onto a handset 5 using a second rear projection screen 2, thereby producing the prosthesis projection 7. Alternatively, the device can propose an endoprosthesis model EM after automatic detection and measurement of relevant anatomical structures (e.g. of the angle between neck and shaft of the femur in the case of hip joint endoprostheses).

In step 102, the user generates a suitable prosthesis projection 7 using a prosthesis projection control unit 15. Alternatively, the device can propose a prosthesis projection 7 which can be calculated from the currently selected anatomy projection 11 and the typical spatial disposition of the endoprosthesis and the anatomical structures surrounding it.

In the subsequent step 103, the user moves or rotates the handset 5 with the prosthesis projection 7 with respect to the anatomy projection 6 until the position of the endoprosthesis fits in the current projection or until he establishes that the endoprosthesis model EM does not fit and he must try an alternative model. The movement of the handset 5 is tracked by the device and the prosthesis projection 7 is always projected into the same region of the handset 5. The fitting can here be assisted by the system by calculating the quality of a fit and providing the user with visual, audible and/or haptic feedback about it via an output channel. The calculation of the quality of a fit requires the extraction of relevant structures (e.g. acetabulum and endoprosthesis contour in the case of hip joint endoprostheses) from the anatomy projection 6 and the prosthesis projection 7 using suitable image processing algorithms (e.g. edge detection) as well as the use of suitable collision and movement planning algorithms. As an alternative to automatic detection of relevant anatomical structures, the user can also mark them with his fingers on the second rear projection screen 2 so that they can be displayed and used by the device.

After successful fitting of the endoprosthesis model EM in the current projection plane, in step 104 using the simultaneous projection control unit 17 the user can simultaneously change the anatomy projection plane and the prosthesis projection plane and check whether the endoprosthesis model EM selected and its position also fit in other projection planes. If so, in step 105 the endoprosthesis model EM selected is documented in a findings report, i.e. stored. In addition, the determined position of the endoprosthesis can be stored in an overlay of the anatomy projection 6. In this way it is possible to check intra- or postoperatively the positioning of the endoprosthesis by comparing the planned position with the actual position, e.g. using registration algorithms.

If the user is unable to fit the endoprosthesis model EM selected, in step 105 he can select a different slice plane through the endoprosthesis using the prosthesis projection control unit 15 and thus rotate the endoprosthesis in space with respect to the anatomy and attempt a new fit as per steps 103, 104.

The device and method described enable the user to select an endoprosthesis to be projected onto the handset 5, to specify its position in space and also a slice plane through it, and to move/rotate the handset 5 until a suitable endoprosthesis has been found that fits. The user does this by moving a physical element, namely the handset 5, with his hands, which means that the method described is much more intuitive and manageable than selecting and fitting an endoprosthesis model EM on a standard VDU workstation using a computer mouse. Moreover, the method has much in common with fitting by moving endoprosthesis templates over a printed-out X-ray image.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

LIST OF REFERENCE CHARACTERS 1 first rear projection screen
2 second rear projection screen
3 feedback unit
4 control element
5 handset
6 first projection/anatomy projection
7 second projection/prosthesis projection
8 displacement unit
11 first projection unit
12 second projection unit
13 anatomy projection control unit
14 prosthesis selection control unit
15 prosthesis projection control unit
16 zoom control unit
17 simultaneous projection control unit
100 generating a first projection 6
101 selecting an endoprosthesis model EM
102 generating a second projection 7
103 shifting and/or rotating
104 simultaneously changing/selecting a slice plane
105 storing
EM endoprosthesis model

What is claimed is:

1. A device for the pre-operative selection and determination of a position of an endoprosthesis, comprising:
a fixed first rear projection screen with variable opacity;
a movable second rear projection screen, located in front of the fixed first rear projection screen with respect to rear projection;
a processor configured to implement:
a first projection unit configured to generate at least one first projection, of a region of a subject in which an endoprosthesis is to be fitted, onto the fixed first rear projection screen; and
a second projection unit configured to generate at least one second projection of the endoprosthesis onto the movable second rear projection screen, scaling of the at least one first and at least one second projection being identical.

2. The device as claimed in claim 1, wherein the at least one second projection takes place through the fixed first rear projection screen by varying the opacity thereof.

3. The device as claimed in claim 2, wherein the processor is further configured to implement a displacement unit configured to at least one of displace and rotate the second rear projection screen or the at least one second projection with respect to the first rear projection screen.

4. The device as claimed in claim 1, wherein the processor is further configured to implement a displacement unit configured to at least one of displace and rotate the movable second rear projection screen or the at least one second projection with respect to the fixed first rear projection screen.

5. The device as claimed in claim 4, wherein the displacement unit comprises a feedback unit configured to provide a resistive force for displacing the movable second rear projection screen or by which the at least one second projection is variable.

6. The device as claimed in claim 1, wherein the at least one first projection is a two-dimensional projection of a captured image or image slice of a region of interest.

7. The device as claimed in claim 1, wherein the at least one second projection is a two-dimensional projection of at least one of a pictorial and geometric slice representation of the endoprosthesis.

8. The device as claimed in claim 1, wherein at least one of
the at least one first projection is generatable from an X-ray photograph or a slice of a tomography dataset, and
the at least one second projection is generateable from a three-dimensional geometry dataset of the endoprosthesis.

9. The device as claimed in claim 1, wherein the processor is further configured to implement a prosthesis projection control unit configured to select the at least one first and at least one of second projection such that they have a common image capture plane.

10. The device as claimed in claim 1, wherein the processor is further configured to implement a zoom control unit configured to simultaneously zoom the at least one first and at least one second projection.

11. The device as claimed in claim 1, wherein the processor is further configured to implement a simultaneous projection control unit configured to at least one of simultaneously change and select an image capture plane of the at least one first and at least one second projection.

12. The device as claimed in claim 1, wherein the processor is further configured to implement a prosthesis selection control unit configured to select an endoprosthesis from stored data.

13. A method for the pre-operative selection and determination of a position of an endoprosthesis, the method comprising:
generating at least one first projection of a region of a subject in which an endoprosthesis is to be fitted, onto a first rear projection screen; and
generating at least one second projection of the endoprosthesis onto a movable second rear projection screen through the first rear projection screen, scaling of the at least one first and at least one second projection being identical.

14. The method as claimed in claim 13, further comprising:
at least one of displacing and rotating the second rear projection screen or the at least one second projection with respect to the first rear projection screen such that the at least one second projection is fittable into the at least one first projection.

15. The method as claimed in claim 14, further comprising:
storing a designation of the endoprosthesis and its position with respect to the at least one first projection.

* * * * *